US008890090B2

(12) United States Patent
Inoue

(10) Patent No.: US 8,890,090 B2
(45) Date of Patent: Nov. 18, 2014

(54) LINE SCANNING APPARATUS UTILIZING IRRADIATION POSITION AND STATIONARY TIME FOR SCANNING CONTROL

(75) Inventor: Junichi Inoue, Niihama (JP)

(73) Assignee: Sumitomo Heavy Industries, Ltd., Tokyo (JP)

(*) Notice: Subject to any disclaimer, the term of this patent is extended or adjusted under 35 U.S.C. 154(b) by 0 days.

(21) Appl. No.: 13/047,334

(22) Filed: Mar. 14, 2011

(65) Prior Publication Data

US 2011/0220807 A1    Sep. 15, 2011

(30) Foreign Application Priority Data

Mar. 15, 2010    (JP) ................ P2010-057639

(51) Int. Cl.
*A61N 5/00* (2006.01)
*A61N 5/10* (2006.01)
*G21K 1/093* (2006.01)

(52) U.S. Cl.
CPC ............ *A61N 5/1042* (2013.01); *A61N 5/1043* (2013.01); *A61N 5/1048* (2013.01); *A61N 2005/1087* (2013.01); *G21K 1/093* (2013.01)
USPC ................................ 250/492.1

(58) Field of Classification Search
USPC ................ 250/306, 307, 311, 492.1, 492.2, 250/492.22, 504 R, 493.1
See application file for complete search history.

(56) References Cited

U.S. PATENT DOCUMENTS

| | | | |
|---|---|---|---|
| 6,407,397 B1 * | 6/2002 | Seto ................. | 250/492.22 |
| 6,600,164 B1 * | 7/2003 | Badura et al. ............. | 250/492.3 |
| 6,670,618 B1 | 12/2003 | Hartmann et al. | |
| 6,929,892 B2 * | 8/2005 | Shishido et al. ................. | 430/30 |
| 2002/0145113 A1 * | 10/2002 | Sullivan et al. ............... | 250/311 |

(Continued)

FOREIGN PATENT DOCUMENTS

| | | |
|---|---|---|
| JP | 2004-065808 A | 3/2004 |
| JP | 2006-034701 A | 2/2006 |

(Continued)

OTHER PUBLICATIONS

European Search Report dated Jun. 8, 2013 issued in corresponding Application No. EP 11002104.5.

(Continued)

*Primary Examiner* — Michael Logie
*Assistant Examiner* — Jason McCormack
(74) *Attorney, Agent, or Firm* — Squire Patton Boggs (US) LLP

(57) ABSTRACT

The invention includes an irradiation nozzle which radiates a line scanning beam, an irradiation position sensor which detects an irradiation position of the line scanning beam, an arithmetic processing circuit unit which measures the stationary time of the line scanning beam at the irradiation position detected by the irradiation position sensor, and an irradiation control unit which performs scanning control of the line scanning beam by utilizing the irradiation position measured by the irradiation position sensor and the stationary time detected by the arithmetic processing circuit unit. According to this line scanning apparatus, scanning control of the line scanning beam is performed by utilizing the irradiation position of the beam and the stationary time corresponding to the irradiation position, so that irradiation of the beam to an erroneous position or excessive irradiation of the line scanning beam can be more reliably prevented, and thereby the reliability of the line scanning apparatus can be improved.

6 Claims, 9 Drawing Sheets

(56) References Cited

U.S. PATENT DOCUMENTS

| | | |
|---|---|---|
| 2003/0029998 A1* | 2/2003 | Matsumoto et al. .......... 250/307 |
| 2004/0173763 A1* | 9/2004 | Moriyama et al. ......... 250/492.1 |
| 2004/0227104 A1 | 11/2004 | Matsuda et al. |
| 2004/0233407 A1* | 11/2004 | Nishi et al. ...................... 355/53 |
| 2006/0033042 A1* | 2/2006 | Groezinger et al. ....... 250/492.1 |
| 2006/0102856 A1* | 5/2006 | Matsuda et al. ......... 250/492.22 |
| 2009/0039256 A1* | 2/2009 | Fujii et al. ..................... 250/306 |
| 2009/0114849 A1* | 5/2009 | Schneider et al. ......... 250/492.1 |
| 2009/0314960 A1* | 12/2009 | Balakin ...................... 250/492.3 |

FOREIGN PATENT DOCUMENTS

| | | |
|---|---|---|
| JP | 2009-243891 A2 | 10/2009 |
| JP | 2008054973 A | 3/2013 |
| WO | WO 2009135879 A1 * | 11/2009 |

OTHER PUBLICATIONS

European Search Report application No. 11002104.5 dated Aug. 6, 2013.

Japanese Office Action application No. P2010-057639 dated Feb. 12, 2014.

* cited by examiner

LINE SCANNING APPARATUS UTILIZING IRRADIATION POSITION AND STATIONARY TIME FOR SCANNING CONTROL

RELATED APPLICATION

Priority is claimed to Japanese Patent Application No. 2010-057639, filed Mar. 15, 2010, the entire content of which is incorporated herein by reference.

BACKGROUND

1. Technical Field

The present invention relates to a line scanning apparatus which performs scanning control of a line scanning beam.

2. Description of the Related Art

As a related art in such a field, a charged particle beam irradiation apparatus includes a scanning electromagnet for performing scanning of a charged particle beam, control device which controls the operation of the scanning electromagnet, and a monitor which detects the position of a beam, and performs continuous irradiation while performing scanning of the charged particle beam along an irradiation line of an irradiation field set in an object to be irradiated.

SUMMARY

According to an embodiment of the invention, there is provided a line scanning apparatus including a beam irradiation unit which radiates a line scanning beam, an irradiation position detection unit which detects an irradiation position of the line scanning beam, a stationary time measuring unit which measures the stationary time of the line scanning beam at the irradiation position detected by the irradiation position detection unit, and a scanning control unit which performs scanning control of the line scanning beam by utilizing the irradiation position detected by the irradiation position detection unit and the stationary time measured by the stationary time measuring unit.

DETAILED DESCRIPTION

In the irradiation apparatus as described above, it is necessary to avoid a situation where parts other than an irradiation field are irradiated with a charged particle beam or a situation where the same part is excessively irradiated. For this reason, an irradiation apparatus with high reliability which can perform high-precision control of a charged particle beam is required.

Thus, it is desirable to provide a line scanning apparatus which can improve reliability.

According to the line scanning apparatus related to the embodiment of the invention the irradiation position of the line scanning beam is detected and the stationary time corresponding to the irradiation position is measured, and scanning control of the line scanning beam is performed by utilizing these results, so that irradiation of the line scanning beam to an erroneous position or excessive irradiation of the line scanning beam can be more reliably prevented, and thereby the reliability of the line scanning apparatus can be improved.

The line scanning apparatus related to the embodiment of the invention may further include an interlock control unit which performs interlock control by utilizing the irradiation position detected by the irradiation position detection unit and the stationary time measured by the stationary time measuring unit.

In this case, if the line scanning beam is radiated to an erroneous position or is excessively radiated so as to exceed a predetermined time, the erroneous irradiation of the line scanning beam can be prevented by performing the interlock control of stopping the irradiation of the line scanning beam.

Additionally, in the line scanning apparatus related to the embodiment of the invention, the scanning control unit may perform feedback control of scanning of the line scanning beam by utilizing the irradiation position detected by the irradiation position detection unit and the stationary time measured by the stationary time measuring unit.

In this case, high-precision scanning control of a line scanning beam is realized by the feedback control, and thereby the reliability of a line scanning apparatus can be improved.

Hereinafter, a line scanning apparatus related to a preferred embodiment of the invention will be described in detail with reference to the drawings.

Figure 1:
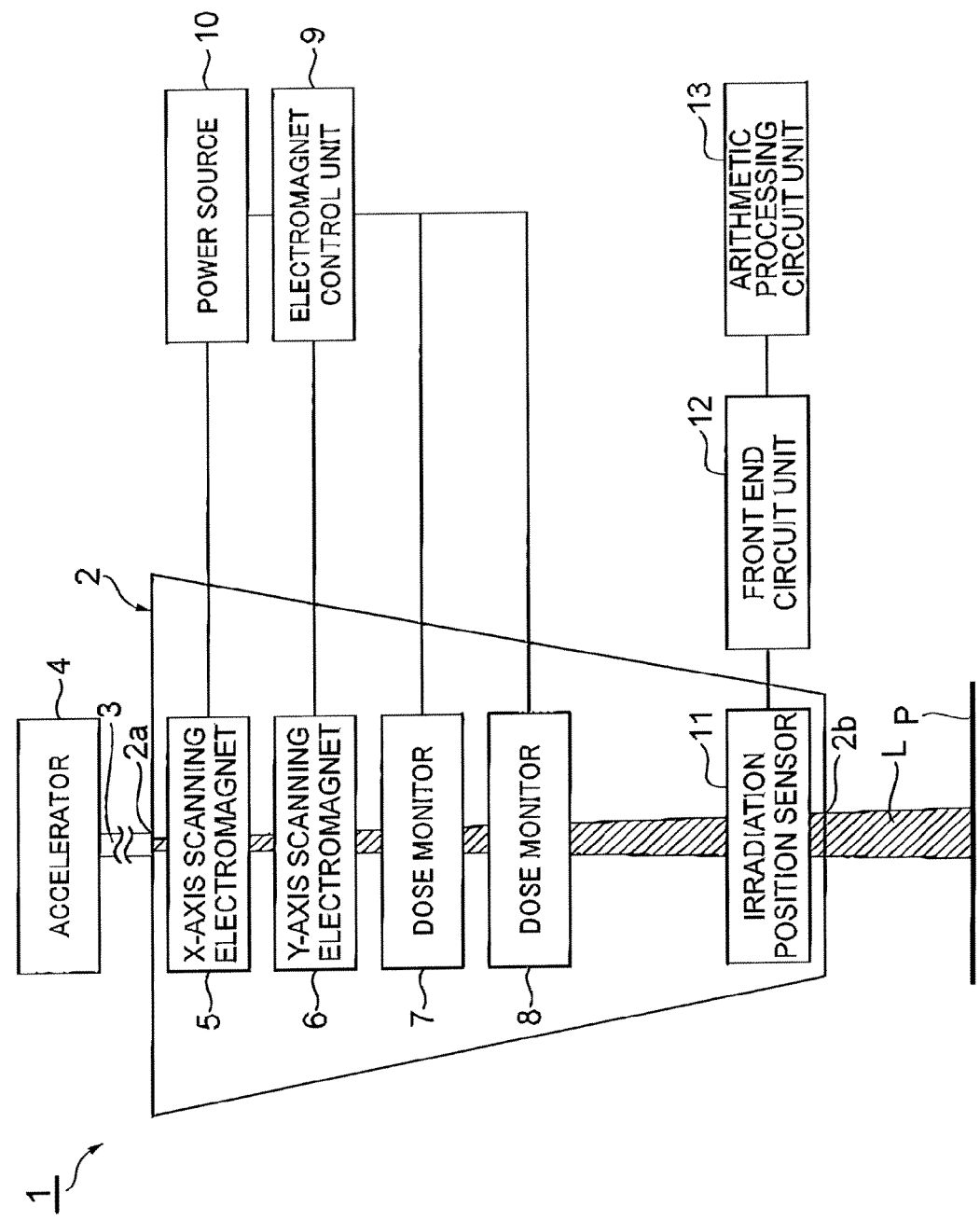
FIG. 1 is a configuration diagram showing a line scanning apparatus related to an embodiment of the invention.

As shown in FIG. 1, the line scanning apparatus 1 related to the present embodiment is utilized in a particle beam therapy facility which performs scanning of line scanning beams, such as a proton beam and a carbon ion beam, thereby irradiating a affected part of a patient to perform cancer treatment or the like, and controls the scanning of the line scanning beams. The line scanning apparatus 1 includes an irradiation nozzle (beam irradiation means) 2 which irradiates an irradiation field set in an affected part of a patient with a line scanning beam. In the particle beam therapy using such a line scanning beam, in order to reduce a risk due to erroneous irradiation of the line scanning beam, medical treatment proceeds by irradiating the inside of the irradiation field a plurality of times with a beam with suppressed intensity.

The irradiation nozzle 2 is connected to an accelerator 4 through a beam transport system 3. The accelerator 4 is a cyclotron, a synchrotron, or the like which accelerates charged particles, such as a proton and a carbon ion. Charged particles accelerated by the accelerator 4 are shaped into a pencil beam with a diameter of several millimeters, and enter the beam transport system 3. A beam L of the charged particles, which is supplied to a supply port 2a of the irradiation nozzle 2 through the beam transport system 3, is emitted from an irradiation port 2b at the tip of irradiation nozzle 2, and an irradiation field P set in an affected part of a patient is irradiated with the beam.

Scanning electromagnets 5 and 6 for deflecting the supplied beam L to control scanning are provided within the irradiation nozzle 2. The scanning electromagnets 5 and 6 are configured so that scanning of the beam L can be performed in two directions orthogonal to each other within a plane perpendicular to the direction straight ahead of the supplied beam L. The two directions orthogonal to each other within a plane perpendicular to the direction straight ahead of the beam L are defined as an X-axis direction and a Y-axis direction. The scanning electromagnet 5 is an X-axis scanning electromagnet which deflects the beam L in the X-axis direction, and the scanning electromagnet 6 is a Y-axis scanning electromagnet which deflects the beam L in the Y-axis direction. The beam L is deflected within the plane orthogonal to the direction straight ahead by the scanning electromagnets 5 and 6, and is scanned as a line scanning beam.

Two dose monitors 7 and 8 are provided within the irradiation nozzle 2 so as to intersect the course of the beam L. The dose monitors 7 and 8 are provided closer to the irradiation port 2b than the scanning electromagnets 5 and 6, and detect the dose of the passing beam L. The dose monitors 7 and 8 output the detected dose to an electromagnet control unit 9.

The electromagnet control unit 9 is provided outside the irradiation nozzle 2, and is electrically connected to the scanning electromagnets 5 and 6, the dose monitors 7 and 8, and a power source 10 which supplies an electric current thereto. Additionally, the electromagnet control unit 9 is electrically connected to an irradiation control unit (scanning control means) 14 which supervises the control relating to the irradiation of the beam L (refer to FIG. 3). The electromagnet control unit 9 outputs detection results of the dose monitors 7 and 8 to the irradiation control unit 14. The electromagnet control unit 9 controls the scanning electromagnets 5 and 6 according to instructions from the irradiation control unit 14 so that scanning of the beam L is performed along a scanning pattern which will be described later.

Figure 2:
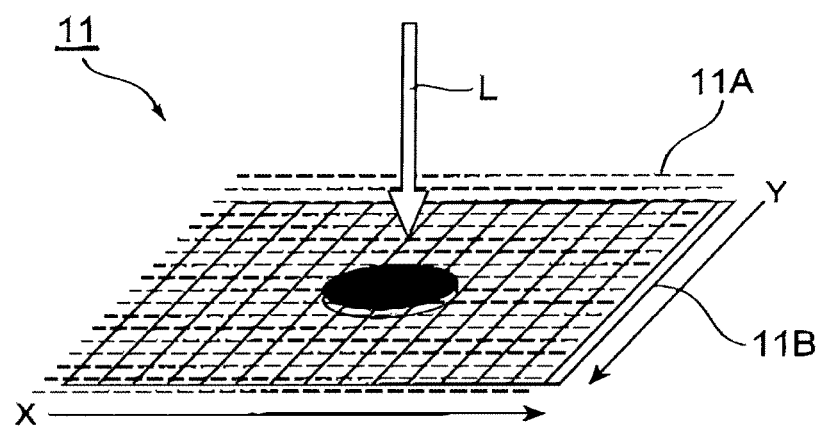
FIG. 2 is a view for describing the configuration of an irradiation position sensor of FIG. 1.

As shown in FIGS. 1 and 2, an irradiation position sensor (irradiation position detecting means) 11 which detects the irradiation position of the beam L is provided within the irradiation nozzle 2. The irradiation position sensor 11 is provided closer to the irradiation port 2b than the dose monitors 7 and 8. The irradiation position sensor 11 is supplied with a high voltage from the power source 10, and includes transmissive multi-strip wires 11A and 11B built into an ionization chamber.

128 lengths of each of the wires 11A and 11B are provided, and the wires 11A and 11B constitute a wire grid which forms a grid shape as seen from the direction straight ahead of the beam L. The wires 11A are arranged so as to extend in the above-described X-axis direction, and the wires 11B are arranged so as to extend in the above-described Y-axis direction. The wires 11A and the wires 11B are arranged so that the heights thereof are different from each other in the direction straight ahead of the beam L. In addition, the number of the wires 11A and 11B is not limited to 128, and may be less than or more than 128.

In the wires 11A and 11B configured in this way, their positions within the plane can be expressed as coordinates using respective intersections of the wires 11A and 11B as seen from the direction straight ahead of the beam L. Since charges are generated within the wires 11A and 11B which have received the irradiation of the beam L, the distribution of intersections, i.e., the irradiation position of the beam L, included within an irradiation range of the beam L can be detected by detecting the charges.

Figure 3:
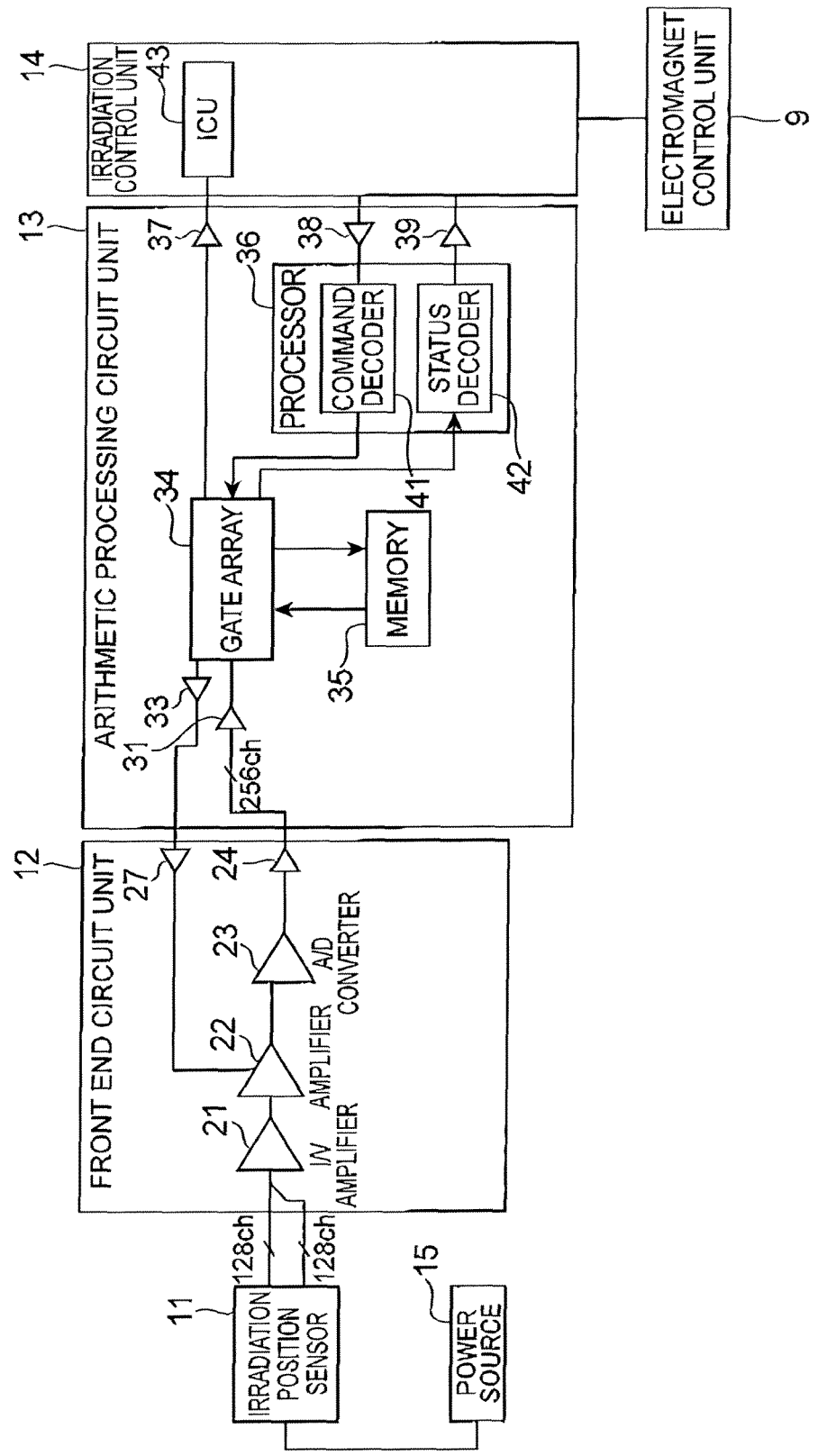
FIG. 3 is a functional block diagram showing the functional configuration of the line scanning apparatus.
Figure 4:
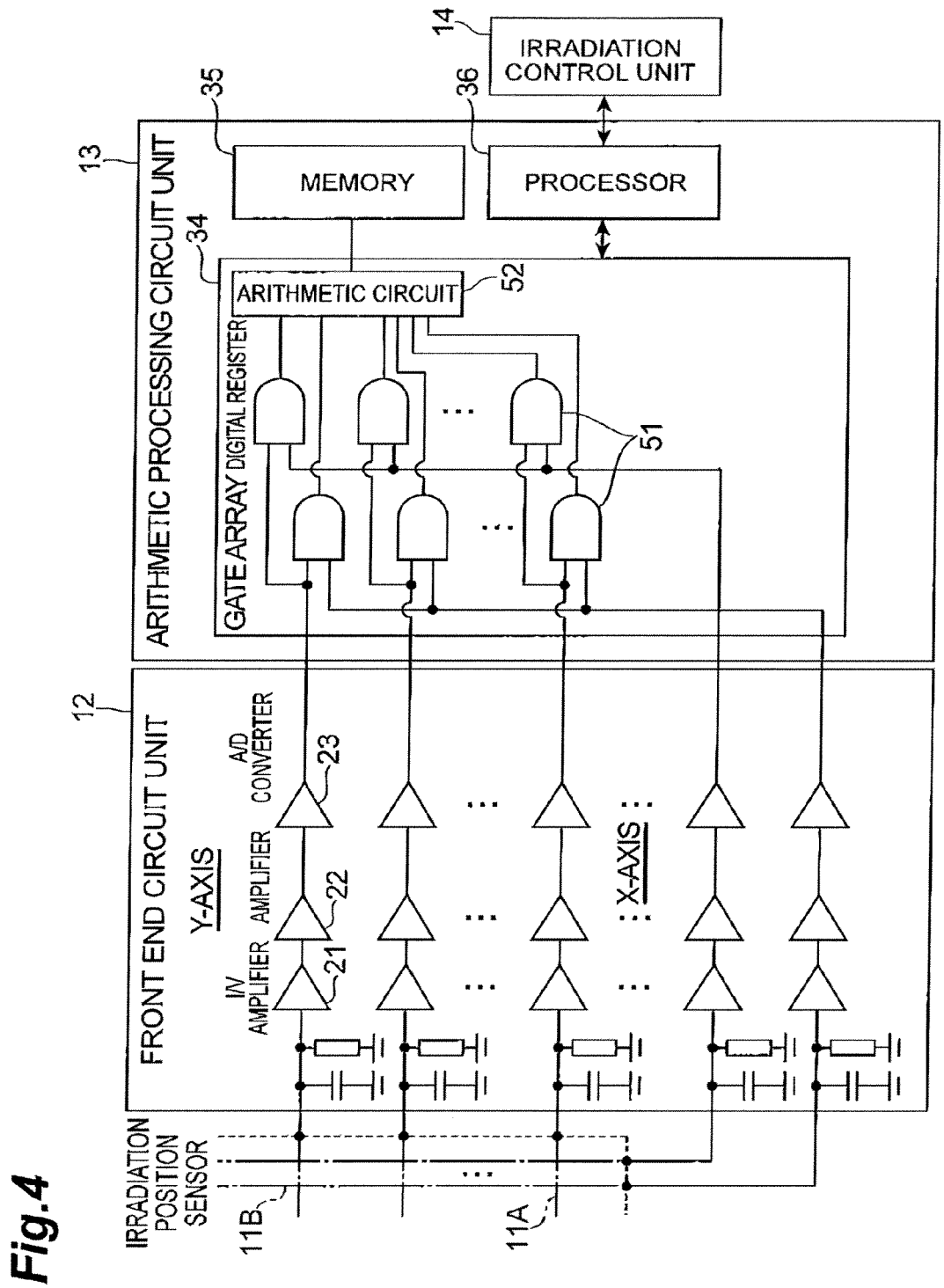
FIG. 4 is a view showing a front end circuit unit and an arithmetic processing circuit unit of FIG. 1.

As shown in FIGS. 1, 3, and 4, the irradiation position sensor 11 is electrically connected to an arithmetic processing circuit unit (stationary time measuring means) 13 via a front end circuit unit 12. The front end circuit unit 12 has 128×2 (256) of each of I/V amplifiers 21, amplifiers 22, and A/D converters 23. The I/V amplifiers 21, the amplifiers 22, and the A/D converters 23 are serially connected to the wires 11A and 11B of the irradiation position sensor 11 in a one-to-one correspondence.

If charges are generated in the wires 11A and 11B by the irradiation of the beam L in the front end circuit unit 12, an electric current flows into the I/V amplifier 21 connected to each of the wires 11A and 11B, and is converted into a voltage signal by the I/V amplifier 21. Thereafter, the voltage signal is amplified by the amplifier 22, and the amplified voltage signal is input to the A/D converter 23. Additionally, a signal output from a gate array 34 of an arithmetic processing circuit unit 13 is input to the amplifier 22 through a transceiver 33 and a receiver 27.

The A/D converter 23 converts the signal input by the amplifier 22 into a digital signal, and outputs the converted digital signal. The digital signal output by the A/D converter 23 is sent to the gate array 34 of the arithmetic processing circuit unit 13 through a transceiver 24. In addition, in the front end circuit unit 12, signal processing is performed every 0.2 ms, and thereby the detection accuracy of the irradiation position of the beam L is secured.

The arithmetic processing circuit unit 13 has the gate array 34, a memory 35, and a processor 36. The gate array 34 has a data register 51 and an arithmetic circuit 52. In the gate array 34, the digital signal output from the A/D converter 23 is input to the data register 51 through a receiver 31.

The data registers 51 numbering 128×128 (16,384) are arranged corresponding to respective intersections of the wires 11A and 11B as seen from the direction straight ahead of the beam L. The A/D converters 23 corresponding to each of the wires 11A and the wires 11B are connected to the input terminal of each data register 51. If an intersection of the corresponding wires 11A and 11B is irradiated with the beam L, one digital signal at a time is input from each of the A/D converters 23 connected to the input terminal, thereby satisfying an output condition, and an irradiation position signal is output from the data register 51. The irradiation position signal output from the data register 51 is sent to the arithmetic circuit 52.

In the arithmetic circuit 52, the position of an intersection of the wires 11A and 11B which has received the irradiation of the beam L is detected from the irradiation position signal output from the data register 51, and the detection result is temporarily stored as irradiation position information. As such, in the gate array 34, the irradiation position of the beam L is detected in real time on the basis of electric currents output from each of the wires 11A and 11B of the irradiation position sensor 11. The gate array 34 calculates the center of the irradiation position of the detected beam L as the center-of-gravity position. Additionally, the gate array 34 measures the stationary time of the beam L at every calculated center-of-gravity position.

Scanning patterns relating to the scanning control of the beam L are stored in the memory 35. The scanning patterns are scanning patterns of the beam L to the irradiation field set in the affected part of a patient, and include information on the irradiation position, stationary time, and locus of the center-of-gravity position of the beam L. The memory 35 outputs a requested scanning pattern to the gate array 34.

The gate array 34 compares the scanning pattern with the irradiation position and stationary time of the detected beam L, thereby performing an abnormality existence determination of whether or not scanning control of the beam L is out of the range of the scanning pattern. If it is determined that the scanning control of the beam L is out of the range of the scanning pattern, the gate array 34 outputs an interlock signal to an ICU (Irradiation Control Unit) (interlock control means) 43 of the irradiation control unit 14 via a transceiver 37. The ICU 43 performs the interlock of stopping the irradiation of the beam L compulsorily if an interlock signal is output from the gate array 34.

The processor 36 has a command decoder 41 to which a signal from the irradiation control unit 14 is input, and a status encoder 42 which outputs a signal to the irradiation control unit 14. A synchronizing signal for synchronizing with the irradiation control unit 14 is input to the command decoder 41 through a receiver 38. The command decoder 41 outputs the input synchronizing signal to the gate array 34. The irradiation position of the beam L detected by the gate array 34 is input to the status encoder 42. The status encoder 42 outputs the irradiation position of the input beam L to the irradiation control unit 14.

Figure 5:
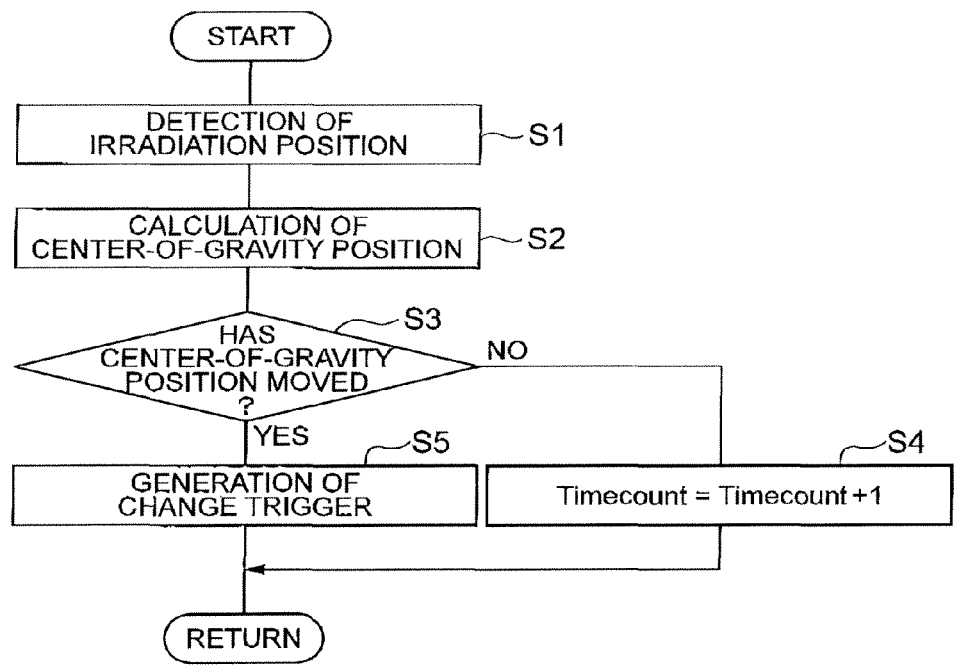
FIG. 5 is a flow chart showing actual measurement value output processing in the arithmetic processing circuit unit.
Figure 6:
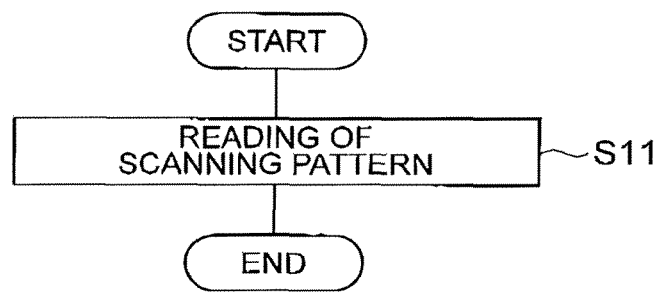
FIG. 6 is a flow chart showing scanning pattern output processing in the arithmetic processing circuit unit.
Figure 7:
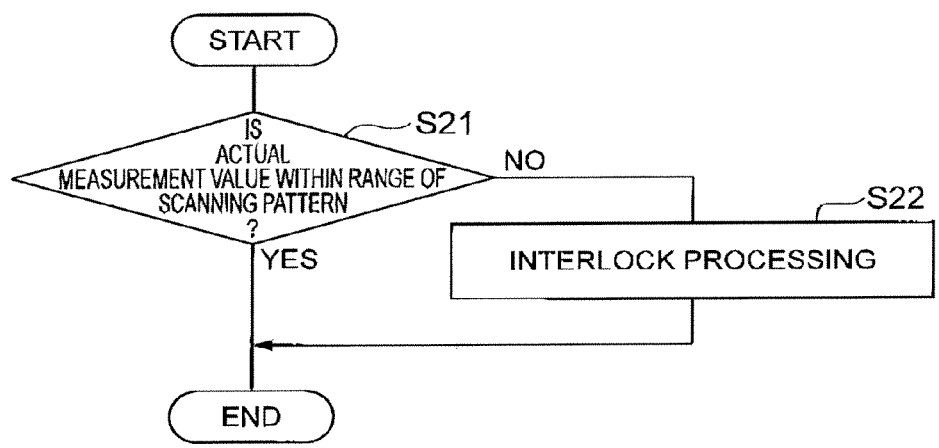
FIG. 7 is a flow chart showing abnormality existence determination processing in the arithmetic processing circuit unit.

Next, abnormality existence determination processing of the scanning control of the beam L in the arithmetic processing circuit unit 13 will be described with reference to the drawings. FIG. 5 is a flow chart showing output processing of actual measurement values in the arithmetic processing circuit unit 13, and FIG. 6 is a flow chart showing output processing of scanning patterns in the arithmetic processing circuit unit 13. FIG. 7 is a flow chart showing abnormality existence determination processing in the arithmetic processing circuit unit 13.

As shown in FIG. 5, in the arithmetic processing circuit unit 13 (gate array 34), first, the irradiation position of the beam L is detected by utilizing a digital signal output from the front end circuit unit 12 according to an electric current generated in the irradiation position sensor 11 (Step S1). Thereafter, the center of the irradiation position of the beam L is calculated as the center-of-gravity position (Step S2).

When the center-of-gravity position is calculated, the calculated center-of-gravity position is compared with a previously calculated center-of-gravity position, and it is determined whether or not the center-of-gravity position has moved (Step S3). If it is determined that the center-of-gravity position has not moved, the value of Timecount at the center-of-gravity position concerned is increased by one (Step S4). Thereafter, the processing returns to Step S1 from which the respective steps are repeated. In addition, if calculation of the center-of-gravity position is being calculated for the first time, it is determined that the center-of-gravity position has moved. Additionally, the initial value of Timecount is set to "0".

On the other hand, if it is determined that the center-of-gravity position has moved, a change trigger for performing reading of a scanning pattern which will be described later is generated (Step S5). Additionally, Timecount is reset and counting is again started from "0". Thereafter, the processing returns to Step S1 from which the respective steps are repeated.

As shown in FIG. 6, if a change trigger is generated in Step S4 shown in FIG. 5, in the arithmetic processing circuit unit 13 (gate array 34), read-out of a scanning pattern corresponding to the center-of-gravity position is performed from the memory 35 (Step S11). When the read-out of the scanning pattern is performed, processing is ended at this time until a change trigger is generated again.

As shown in FIG. 7, if a change trigger is generated in Step S5 shown in FIG. 5, in the arithmetic processing circuit unit 13 (gate array 34), abnormality existence determination of whether or not the center-of-gravity position calculated in Step S2 is within the range of the scanning pattern is performed (Step S21). The scanning pattern to be used in this Step S21 is updated whenever reading of a scanning pattern is performed in Step S11 of FIG. 6.

If the center-of-gravity position calculated in Step S2 is within the range of the scanning pattern, that is, if the detected irradiation position coincides with the irradiation position of the scanning pattern, the measured stationary time is less than or equal to the stationary time specified in the scanning pattern, and the locus of movement of the center-of-gravity position is within the range of a locus specified in the scanning pattern, it is determined that scanning control of the beam L is being performed normally. If it is determined that the scanning control of the beam L is being performed normally, the arithmetic processing circuit unit 13 ends the processing.

On the other hand, if an actual measurement value is not within the range of the scanning pattern, that is, if a detected irradiation position is different from the irradiation position of the scanning pattern, a measured stationary time exceeds a stationary time specified in the scanning pattern, or the locus of movement of the center-of-gravity position is out of the range of the locus specified in the scanning pattern, it is determined that there is an abnormality in the scanning control of the beam L. Interlock processing is performed if it is determined that there is an abnormality in the scanning control of the beam L (Step S22). In the interlock processing, an interlock signal is generated, and output to the ICU 43 of the irradiation control unit 14, and thereafter, the subsequent is ended. The ICU 43 to which the interlock signal has been output performs the interlock of stopping the irradiation of the beam L compulsorily.

Figure 8:
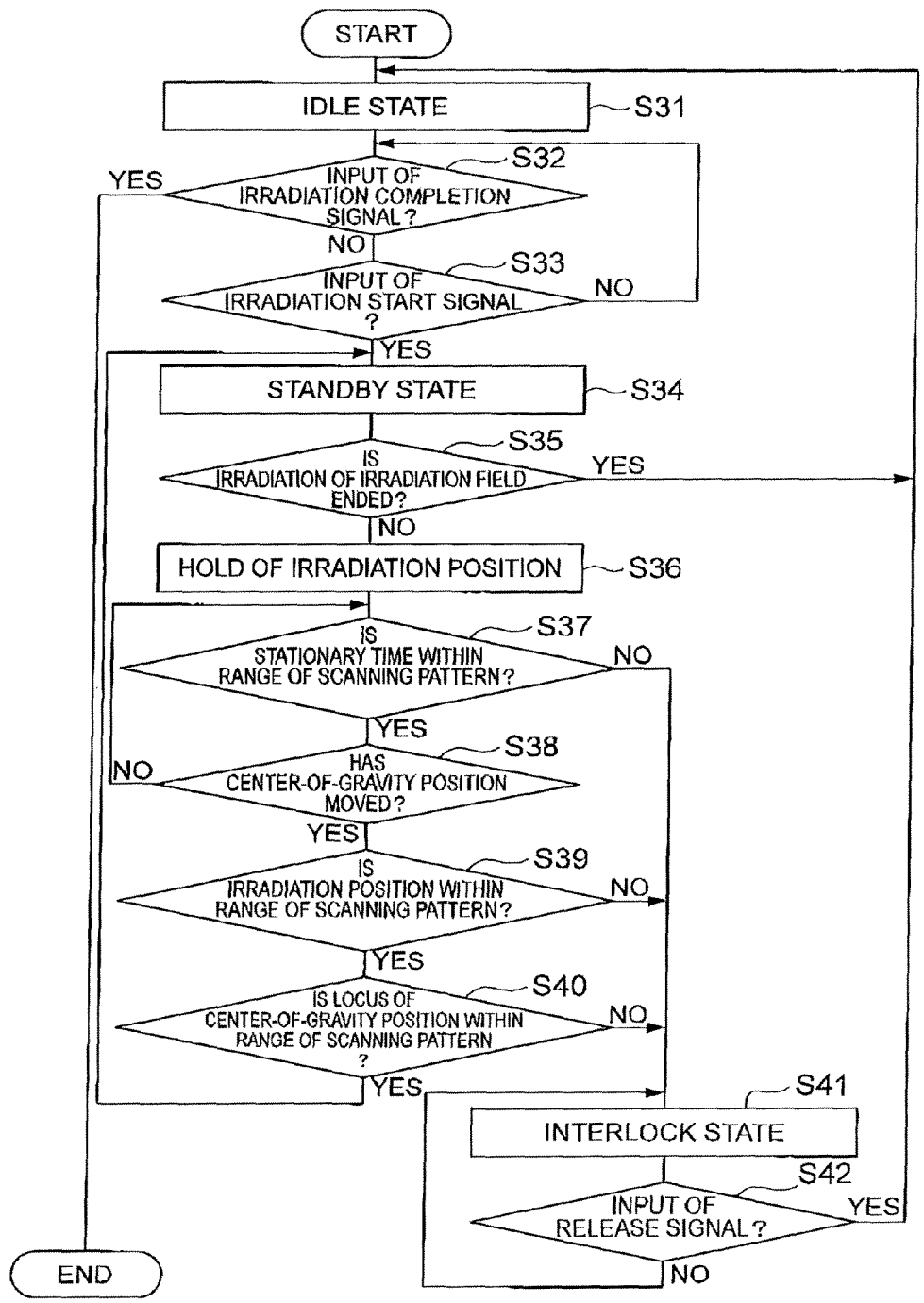
FIG. 8 is a flow chart showing the state transition of the line scanning apparatus.

Next, the state transition in the line scanning apparatus 1 will be described with reference to the drawings. FIG. 8 is a state transition diagram of the line scanning apparatus.

As shown in FIG. 8, the line scanning apparatus 1 is transferred to an idle state when operation preparation is ended after being activated (Step S31). In the idle state, it is first determined whether or not an irradiation completion signal has been input by a medical practitioner, such as a doctor, or a completion program (Step S32). If it is determined that the irradiation completion signal has been input, the line scanning apparatus 1 ends its operation.

On the other hand, if it is determined that the irradiation completion signal has not been input, it is subsequently determined whether or not an irradiation start signal has been input (Step S33). If it is determined that an irradiation start signal has not been input, the processing returns to Step S32 where the idle state is continued. If it is determined that the irradiation start signal has been input, the processing is transferred to a standby state (Step S34).

When the processing is transferred to the standby state, it is determined whether or not scanning control of the beam L to the irradiation field has ended (Step S35). If it is determined that the scanning control of the beam L to the irradiation field has ended, the processing returns to Step S31 and is transferred to the idle state. On the other hand, if it is determined that the scanning control of the beam L to the irradiation field has not ended, the processing is transferred to a hold state where the irradiation position of the beam L is held after 0.2 ms has elapsed since the transition to the standby state (Step S36).

Thereafter, the center-of-gravity position in the held irradiation position is calculated, the counting of the stationary time at the center-of-gravity position is started, and the processing is transferred to a stationary time determination state where whether or not this stationary time is within the range of the scanning pattern is determined (step S37). If it is determined that the stationary time is not within the range of the scanning pattern, the processing is transferred to Step S41. If it is determined that the stationary time is within the range of the scanning pattern, it is determined whether or not the center-of-gravity position has moved (Step S38).

In Step S38, if it is determined that the center-of-gravity position has not moved, the counting of the stationary time proceeds, and the processing returns to Step S38 where it is determined whether or not the new stationary time is within the range of the scanning pattern. On the other hand, if it is determined that the center-of-gravity position has moved, the processing is transferred to a position determination state where whether or not the irradiation position of the detected beam L is within the range of the scanning pattern is determined (Step S39).

In Step S39, if it is determined that the irradiation position of the beam L is not within the range of the scanning pattern, the processing shifts to Step S41. On the other hand, if it is determined that the irradiation position of the beam L is within the range of the scanning pattern, the processing is transferred to a locus determination state where whether or not the locus of the center-of-gravity position is within the range of the scanning pattern is determined (Step S40).

In Step S40, if it is determined that the locus of the center-of-gravity position is within the range of the scanning pattern, the processing returns to Step S34 and is transferred to the standby state. On the other hand, if it is determined that the locus of the center-of-gravity position is not within the range of the scanning pattern, the processing is transferred to Step S41.

In Step S41, it is determined that there is an abnormality in the scanning control as an actual measurement value relating to the scanning control of beam L is not within the range of the scanning pattern, and the processing is transferred to the interlock state of stopping the irradiation of the beam L compulsorily.

If the processing is transferred to the interlock state, it is determined whether or not a release signal has been input (Step S42). If it is determined that the release signal has not been input, the interlock state is continued, and the determination of Step S42 is again performed after a predetermined time. On the other hand, if it is determined that the release signal has been input, the processing returns to Step S31 and is transferred to the idle state.

Next, an example in a case where it is determined that there is an abnormality in the scanning control of the beam L will be described with reference to the drawings.

Figure 9:
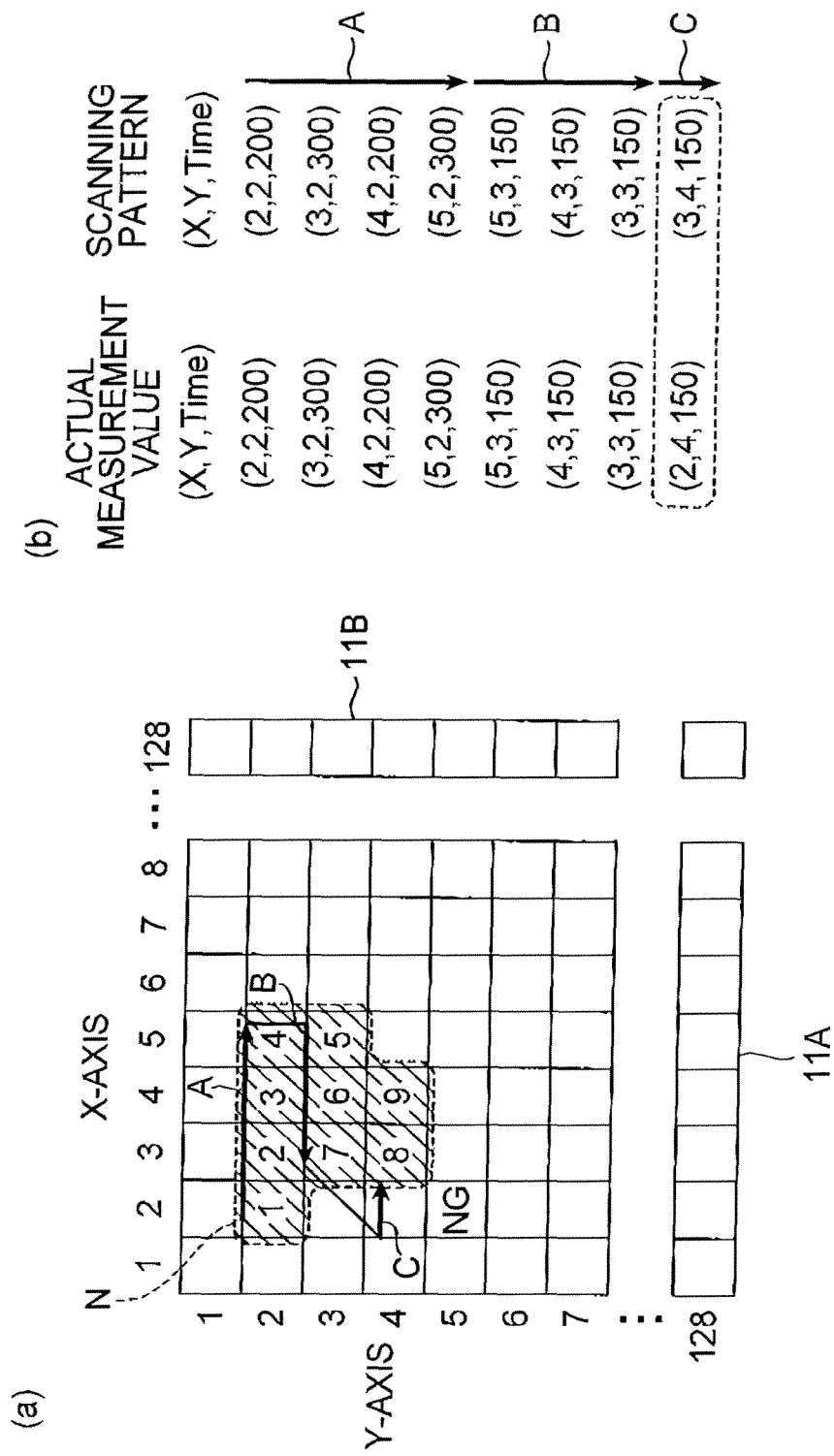
FIG. 9A is a view showing the locus of a line scanning beam.
FIG. 9B is a view for comparing actual measurement values and scanning patterns of FIG. 9A.

As shown in FIG. 9A, a case where scanning control of the beam L is performed in the order of an arrow A, an arrow B, and an arrow C within the irradiation field N will be considered. As for the actual measurement values and scanning patterns in this case, data on the loci of center-of-gravity positions (X-axis, Y-axis) and stationary times (Time) in the respective center-of-gravity positions is shown in FIG. 9B. In addition, in FIG. 9A, a case where not the intersections of the wires 11A and 11B but an irradiation position corresponding to the inside of a frame is detected will be described for clarification of description.

As shown in FIGS. 9A and 9B, as for the scanning between the arrow A in which the center-of-gravity position of the beam L moves to (5, 2) from (2, 2) and the arrows B in which the center-of-gravity position moves to (3, 3) from (5, 3), it is determined that actual measurement values of the loci of the center-of-gravity positions and the stationary time are within the range of the scanning patterns, and the scanning control of beam L is being performed normally. Thereafter in the scanning of the arrow C, the center-of-gravity position (2, 4) which is an actual measurement value is out of the center-of-gravity position (3, 4) in a scanning pattern. Therefore, it is determined that there is an abnormality in the scanning control of the beam L. At this time, in the line scanning apparatus 1, the interlock processing is performed and the scanning of the beam L is compulsorily stopped. Thus, erroneous irradiation of the beam L is prevented further.

According to the line scanning apparatus 1 described above, the irradiation position of the line scanning beam L is detected, the stationary time corresponding to the center-of-gravity position of the irradiation position is measured, and scanning control of the line scanning beam L is performed by utilizing these results, so that irradiation of the line scanning beam L to an erroneous position or excessive irradiation of the line scanning beam can be more reliably prevented, and thereby the reliability of the line scanning apparatus 1 can be improved.

Additionally, in the line scanning apparatus 1, if the line scanning beam L is radiated to an erroneous position, or is excessively radiated so as to exceed a predetermined time, the erroneous irradiation of the line scanning beam can be more reliably prevented by performing the interlock control of stopping the irradiation of the line scanning beam.

The invention is not limited to the above-described embodiment.

For example, the line scanning apparatus 1 may adopt an aspect in which feedback control of scanning of a line scanning beam is performed by utilizing a detected irradiation position and a measured stationary time. Specifically, the line scanning apparatus may adopt an aspect where reset control of a scanning pattern is performed so that an erroneous irradiation is not caused in a part where the erroneous irradiation has occurred once when an irradiation field is irradiated a plurality of times with a beam with suppressed intensity in order to reduce risks due to erroneous operation of a line scanning beam.

Additionally, the line scanning apparatus may also adopt an aspect where, if the center-of-gravity position of a line scanning beam has moved, the stationary time and center-of-gravity coordinates before and after the movement are stored in the arithmetic circuit 13 (gate array 34), the traveling speed of the line scanning beam is calculated using the stationary time and center-of-gravity coordinates before and after the movement, and beam control is performed by feed back of the calculated traveling speed to the electromagnet control unit 9.

Additionally, although the time until the center-of-gravity position of a line scanning beam moves is measured as the stationary time in the above-described embodiment, an aspect may be adopted where the time until not the center-of-gravity position but the irradiation position changes is measured as the stationary time. Additionally, the line scanning apparatus 1 related to the embodiment of the invention can also be applied to equipment or apparatuses other than the particle beam therapy facility.

It should be understood that the invention is not limited to the above-described embodiment, but may be modified into various forms on the basis of the concept of the invention. Additionally, the modifications are included in the scope of the invention.

What is claimed is:

1. A line scanning particle beam therapy apparatus comprising:
    a beam irradiation unit which has an X-axis scanning electromagnet that deflects a charged particle beam in the X-axis direction perpendicular to the direction straight ahead of the charged particle beam, and a Y-axis scanning electromagnet that deflects the charged particle beam in the Y-axis direction perpendicular to the direction straight ahead of the charged particle beam and the X-axis direction, and which radiates the charged particle beam as a line scanning beam;

an irradiation position detection unit which is provided inside the beam irradiation unit and which detects an irradiation position within a plane formed by the X-axis and the Y-axis of the line scanning beam;

a stationary time measuring unit which measures the stationary time of the line scanning beam at the irradiation position detected by the irradiation position detection unit;

a scanning control unit which performs scanning control of the line scanning beam by utilizing the irradiation position detected by the irradiation position detection unit and the stationary time measured by the stationary time measuring unit;

a memory which stores information regarding the irradiation position of the scanning beam, the stationary time of the line scanning beam, and a locus of the line scanning beam;

a calculation processing unit which performs abnormality existence determination by comparing the irradiation position of the line scanning beam, the stationary time of the line scanning beam, and the locus of the line scanning beam, stored in the memory, with the irradiation position detected by the irradiation position detection unit, the stationary time of the line scanning beam measured by the stationary time measuring unit, and the locus of the line scanning beam obtained from a detection result of the irradiation position detection unit; and an interlock control unit which performs interlock control of stopping the irradiation of the line scanning beam, when the calculation processing unit determines an existence of an abnormality.

2. The line scanning particle beam therapy apparatus according to claim 1, wherein the scanning control unit is configured to determine whether or not a center-of-gravity position of the detected line scanning beam has moved, wherein the scanning control unit is configured to determine whether the irradiation position is within a range of a scanning pattern when it is determined that the center-of-gravity position has moved.

3. The line scanning particle beam therapy apparatus according to claim 2, wherein the scanning control unit is configured to determine whether or not a locus of the center-of-gravity position of the detected line scanning beam is within the range of the scanning pattern, wherein the scanning control unit is configured to stop the beam irradiation unit from radiating the charged particle beam when it is determined that the locus of the center-of-gravity position is not within the range of the scanning pattern.

4. The line scanning particle beam therapy apparatus of claim 1, wherein the calculation processing unit compares the center of the irradiation position detected by the irradiation position detection unit and a scanning pattern stored in the memory.

5. The line scanning particle beam therapy apparatus of claim 1, wherein reset control of a scanning pattern is performed in a part where it is determined that the line scanning beam is out of the range of the scanning pattern when the irradiation field is irradiated a plurality of times with the line scanning beam.

6. The line scanning particle beam therapy apparatus of claim 1, wherein the scanning control unit performs feedback control of scanning of the line scanning beam by utilizing the irradiation position measured by the irradiation position detection unit and the stationary time detected by the stationary time measuring unit.

\* \* \* \* \*